US010194816B2

(12) United States Patent
Perschbacher et al.

(10) Patent No.: US 10,194,816 B2
(45) Date of Patent: Feb. 5, 2019

(54) REDUCING FALSE POSITIVES IN DETECTION OF POTENTIAL CARDIAC PAUSES

(71) Applicant: Cardiac Pacemakers, Inc., St. Paul, MN (US)

(72) Inventors: David L. Perschbacher, Coon Rapids, MN (US); Deepa Mahajan, Roseville, MN (US); Krzysztof Z. Siejko, Maple Grove, MN (US); Pramodsingh H. Thakur, Woodbury, MN (US); Keith R. Maile, New Brighton, MN (US); Qi An, Blaine, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 15/449,890

(22) Filed: Mar. 3, 2017

(65) Prior Publication Data

US 2017/0251940 A1    Sep. 7, 2017

Related U.S. Application Data

(60) Provisional application No. 62/304,117, filed on Mar. 4, 2016.

(51) Int. Cl.
*A61B 5/00* (2006.01)
*A61B 5/0402* (2006.01)
(Continued)

(52) U.S. Cl.
CPC .......... *A61B 5/0402* (2013.01); *A61B 5/0022* (2013.01); *A61B 5/0205* (2013.01);
(Continued)

(58) Field of Classification Search
CPC ... A61B 5/0452; A61B 5/0464; A61B 5/0468; A61B 5/0402; A61N 1/362; A61N 1/365; A61N 1/36578
See application file for complete search history.

(56) References Cited

U.S. PATENT DOCUMENTS 4,172,459 A    10/1979    Hepp
4,552,154 A    11/1985    Hartlaub
(Continued)

FOREIGN PATENT DOCUMENTS

WO    WO9965393 A1    12/1999
WO    2009114755 A2    9/2009
WO    2011034468 A1    3/2011

OTHER PUBLICATIONS

International Search Report and Written Opinion issued in PCT/US2017/012641, dated Apr. 24, 2017, 14 pages.
(Continued)

*Primary Examiner* — Scott Getzow (57) ABSTRACT

Embodiments of the disclosure include systems and methods for reducing false positives in detection of pauses. For example, embodiments include a sensing component configured to obtain values of a first physiological parameter and determine a cardiac pause based on the values of the first physiological parameter. Furthermore, embodiments include performing a validation check of the determined cardiac pause using at least one of: the values of the first physiological parameter or values of a second physiological parameter.

20 Claims, 5 Drawing Sheets

(51) Int. Cl.
  *A61B 5/0205* (2006.01)
  *A61B 5/0245* (2006.01)
  *A61B 5/08* (2006.01)
  *A61B 5/16* (2006.01)
  *A61B 7/04* (2006.01)
  *A61N 1/36* (2006.01)
  *A61N 1/39* (2006.01)
  *A61B 7/00* (2006.01)
  *A61B 5/0452* (2006.01)
  *A61B 5/0468* (2006.01)
  *A61B 5/024* (2006.01)

(52) U.S. Cl.
  CPC .......... *A61B 5/0245* (2013.01); *A61B 5/0452* (2013.01); *A61B 5/0468* (2013.01); *A61B 5/0809* (2013.01); *A61B 5/165* (2013.01); *A61B 5/686* (2013.01); *A61B 5/746* (2013.01); *A61B 7/005* (2013.01); *A61B 7/04* (2013.01); *A61N 1/36* (2013.01); *A61N 1/3925* (2013.01); *A61N 1/3962* (2013.01); *A61B 5/024* (2013.01); *A61B 5/0816* (2013.01); *A61N 1/3943* (2013.01)

(56) References Cited

U.S. PATENT DOCUMENTS

| | | |
|---|---|---|
| 5,127,404 A | 7/1992 | Wybory et al. |
| 5,800,466 A | 9/1998 | Routh et al. |
| 5,833,623 A | 11/1998 | Mann et al. |
| 5,902,250 A | 5/1999 | Verrier et al. |
| 5,904,708 A | 5/1999 | Goedeke |
| 6,073,049 A | 6/2000 | Alt et al. |
| 6,076,015 A | 6/2000 | Hartley et al. |
| 6,190,324 B1 | 2/2001 | Kieval et al. |
| 6,490,479 B2 | 12/2002 | Bock |
| 6,804,558 B2 | 10/2004 | Haller et al. |
| 6,890,306 B2 | 5/2005 | Poezevera |
| 6,978,182 B2 | 12/2005 | Mazar et al. |
| 7,146,206 B2 | 12/2006 | Glass et al. |
| 7,395,117 B2 | 7/2008 | Mazar et al. |
| 7,559,903 B2 | 7/2009 | Moussavi et al. |
| 7,751,876 B2 | 7/2010 | Healey |
| 7,996,074 B2 | 8/2011 | Kenknight et al. |
| 8,002,553 B2 | 8/2011 | Hatlestad et al. |
| 8,049,489 B2 | 11/2011 | Gauglitz et al. |
| 8,108,048 B2 | 1/2012 | Masoud |
| 8,126,548 B2 | 2/2012 | Ding et al. |
| 8,145,590 B2 | 3/2012 | Brockway et al. |
| 8,209,011 B2 | 6/2012 | Freeberg |
| 8,396,543 B2 | 3/2013 | Hoeppner et al. |
| 8,423,142 B2 | 4/2013 | Freeberg |
| 8,611,000 B2 | 12/2013 | Komatsu et al. |
| 8,639,318 B2 | 1/2014 | Hatlestad et al. |
| 8,694,116 B2 | 4/2014 | Kenknight et al. |
| 8,731,661 B2 | 5/2014 | White |
| 8,791,815 B2 | 7/2014 | Mazar et al. |
| 8,849,682 B2 | 9/2014 | Mahajan et al. |
| 8,915,741 B2 | 12/2014 | Hatlestad et al. |
| 8,983,603 B2 | 3/2015 | Perschbacher et al. |
| 9,014,807 B2 | 4/2015 | Bocek et al. |
| 9,020,602 B2 | 4/2015 | Aghassian |
| 9,037,240 B2 | 5/2015 | Gunderson |
| 9,610,025 B2 * | 4/2017 | Zhang .................. A61B 5/0464 |
| 2001/0051787 A1 | 12/2001 | Haller et al. |
| 2002/0072783 A1 | 6/2002 | Goedeke et al. |
| 2003/0028080 A1 | 2/2003 | Lebel et al. |
| 2005/0251227 A1 | 11/2005 | Khoo et al. |
| 2005/0288599 A1 | 12/2005 | MacAdam et al. |
| 2007/0255330 A1 | 11/2007 | Lee et al. |
| 2008/0183245 A1 | 7/2008 | van Oort et al. |
| 2009/0058635 A1 | 3/2009 | LaLonde et al. |
| 2009/0063187 A1 | 3/2009 | Johnson et al. |
| 2009/0088821 A1 | 4/2009 | Abrahamson |
| 2010/0057167 A1 | 3/2010 | Evers et al. |
| 2010/0152815 A1 | 6/2010 | Vandanacker |
| 2010/0185251 A1 | 7/2010 | Propato |
| 2010/0280841 A1 | 11/2010 | Dong et al. |
| 2011/0270109 A1 | 11/2011 | Zhang et al. |
| 2012/0029373 A1 | 2/2012 | Stadler et al. |
| 2012/0078131 A1 | 3/2012 | Zong |
| 2012/0154152 A1 | 6/2012 | Rantala et al. |
| 2012/0165887 A1 | 6/2012 | Lee et al. |
| 2012/0188096 A1 | 7/2012 | Corndorf et al. |
| 2012/0232416 A1 | 9/2012 | Gilham et al. |
| 2012/0283544 A1 | 11/2012 | Kraetschmer et al. |
| 2012/0296228 A1 | 11/2012 | Zhang et al. |
| 2013/0274624 A1 | 10/2013 | Mahajan et al. |
| 2014/0277243 A1 | 9/2014 | Maskara et al. |
| 2015/0216433 A1 | 8/2015 | Thakur et al. |
| 2015/0282738 A1 | 10/2015 | Thakur et al. |
| 2015/0342487 A1 | 12/2015 | Thakur et al. |
| 2017/0196457 A1 | 7/2017 | Thakur et al. |
| 2017/0196458 A1 | 7/2017 | Ternes et al. |
| 2017/0199970 A1 | 7/2017 | Stahmann et al. |

OTHER PUBLICATIONS

International Search Report and Written Opinion issued in PCT/US2017/012649, dated Mar. 29, 2017, 18 pages.
International Search Report and Written Opinion issued in PCT/US2017/012651, dated Mar. 24, 2017, 12 pages.
International Search Report and Written Opinion issued in PCT/US2017/020831, dated Jun. 16, 2017, 11 pages.
Passman, Rod S., et al. "Development and Validation of a Dual Sensing Scheme to Improve Accuracy of Bradycardia Pause Detection in an Insertable Cardiac Monitor." Heart Rhythm, 14:1016-1023, 2017.
Sarkar, Shantanu, et al. "A Dual Sensing Scheme to Reduce Inappropriate Detection of Bradycardia and Pauses in an Insertable Cardiac Monitor." 2016 Heart Rhythm, 15 pages.

* cited by examiner

REDUCING FALSE POSITIVES IN DETECTION OF POTENTIAL CARDIAC PAUSES

CROSS-REFERENCE TO RELATED APPLICATION

This application claims priority to Provisional Application No. 62/304,117, filed Mar. 4, 2016, which is herein incorporated by reference in its entirety.

TECHNICAL FIELD

Embodiments of the present disclosure relate to medical systems and devices. More specifically, embodiments of the disclosure relate to reducing false positives in detection of cardiac pauses by a medical system or device.

BACKGROUND

Syncope, also known as fainting, is a temporary loss of consciousness. Typically, syncope is due to a decrease in blood flow to the brain. However, the cause of the decrease in blood flow to the brain may remain unexplained in up to 47% of patients. A possible cause of decrease in blood flow to the brain may be a cardiac pause experienced by a patient. In some cases, a medical device, for example, an implantable cardiac monitor (ICM) or an external cardiac monitor, may be used to determine a potential cardiac pause. For example, the ICM may be implanted under the skin of the chest of a patient to record the heart's electrical activity. The heart's electrical activity, as recorded by the ICM, may be displayed in a graph known as an electrogram (EGM). EGMs may include QRS complexes, which may be analyzed to determine R-R intervals for a patient (e.g., time intervals between QRS complexes). R-R intervals can be used to determine if a cardiac pause has occurred. For example, if an R-R interval exceeds a time threshold, a cardiac pause may have occurred, which may be the underlying cause of syncope for a patient.

SUMMARY

Embodiments of the disclosure include systems and methods for reducing false positives in detection of potential cardiac pauses.

In an Example 1, a system comprises: a sensing component configured to be operatively coupled to a patient and to obtain values of a first physiological parameter of the patient; and at least one processor configured to: determine a potential cardiac pause of the patient using the values of the first physiological parameter; and perform a validation check of the potential cardiac pause using at least one of the values of the first physiological parameter or values of a second physiological parameter.

In an Example 2, the system of Example 1, wherein the values of the first physiological parameter are values of an electrogram of the patient.

In an Example 3, the system of Example 2, wherein the potential cardiac pause is determined when at least one of the following occurs: (1) a first R-R interval of the electrogram is greater than a time threshold, wherein the first R-R interval is identified using a first electric potential, or (2) a subsequent R wave does not occur within a specified period of time after an R wave is identified, wherein the R wave is identified using the first electric potential threshold.

In an Example 4, the system of Example 3, wherein the at least one processor performs the validation check by calculating a second R-R interval and wherein an R wave of the second R-R interval is identified using a second electric potential threshold, the second electric potential threshold being less than the first electric potential threshold.

In an Example 5, the system of any of Examples 1-3, wherein the values of the second physiological parameter are obtained from a heart sound sensor and wherein the at least one processor performs the validation check by determining whether the second physiological parameter includes values indicative of heart sounds following a fiducial of the first physiological parameter.

In an Example 6, the system of Example 5, wherein the heart sounds include at least one of: an S1 heart sound, an S2 heart sound, an S3 heart sound and an S4 heart sound.

In an Example 7, the system of any of Examples 1-6, wherein the at least one processor confirms the validation check by performing at least one of: a morphological analysis of the electrogram and a frequency analysis of the electrogram.

In an Example 8, the system of any of Examples 1-7, wherein the values of the second physiological parameter are obtained from at least one of: a second electrogram, an activity sensor, a posture sensor, a heart sound sensor and an impedance sensor.

In an Example 9, the system of any of Examples 1-8, wherein the at least one processor is configured to be implanted in the patient.

In an Example 10, the system of any of Examples 1-8, wherein the at least one processor is configured to be outside of the patient.

In an Example 11, a method comprises: receiving an indication of a determined potential cardiac pause of the patient, wherein the determined potential cardiac pause is based on a first R-R interval of an electrogram of the patient exceeding a time threshold and wherein an R wave of the first R-R interval is identified using a first electric potential threshold; and performing a validation check of the potential cardiac pause using at least one of: the values of the electrogram or values of a second physiological parameter.

In an Example 12, the method of Example 11, wherein performing the validation check includes computing a second R-R interval of the electrogram during the determined potential cardiac pause, wherein an R wave of the second R-R interval is identified using a second electric potential threshold, the second electric potential threshold being less than the first electric potential threshold.

In an Example 13, the method of Example 12, wherein the first electric potential threshold is at least 33% greater than the second electric potential threshold.

In an Example 14, the method of any of Examples 11-13, further comprising adjusting the first electric potential threshold based on the performed validation check.

In an Example 15, the method of any of Examples 11-14, further comprising confirming the validation check using at least one of: a morphological analysis of the electrogram, a frequency analysis of the electrogram, QRS template matching, activity information, posture information, impedance information, and heart sounds information.

In an Example 16, a system comprises: a sensing component configured to be operatively coupled to a patient and to obtain values of a first physiological parameter; and at least one processor configured to: determine a potential cardiac pause of the patient using the values of the first physiological parameter; and perform a validation check of the potential cardiac pause using at least one of: the values of the first physiological parameter or values of a second physiological parameter.

In an Example 17, the system of Example 16, wherein the values of the first physiological parameter are values of an electrogram.

In an Example 18, the system of Example 17, wherein the potential cardiac pause is determined when at least one of the following occurs: (1) a first R-R interval of the electrogram is greater than a time threshold, wherein the first R-R interval is identified using a first electric potential, or (2) a subsequent R wave does not occur within a specified period of time after an R wave is identified, wherein the R wave is identified using the first electric potential threshold.

In an Example 19, the system of Example 18, wherein the at least one processor performs the validation check by calculating a second R-R interval and wherein an R wave of the second R-R interval is identified using a second electric potential threshold, the second electric potential threshold being less than the first electric potential threshold.

In an Example 20, the system of Example 16, wherein the values of the second physiological parameter are obtained from a heart sound sensor and wherein the at least one processor performs the validation check by determining whether the second physiological parameter includes values indicative of heart sounds following a fiducial of the first physiological parameter.

In an Example 21, the system of Example 20, wherein the heart sounds include at least one of: an S1 heart sound, an S2 heart sound, an S3 heart sound and an S4 heart sound.

In an Example 22, the system of Example 16, wherein the at least one processor is configured to confirm the validation check by performing at least one of: a morphological analysis of the electrogram and a frequency analysis of the electrogram.

In an Example 23, the system of Example 16, wherein the values of the second physiological parameter are obtained from at least one of the following: a second electrogram, an activity sensor, a posture sensor, a heart sound sensor and an impedance sensor.

In an Example 24, the system of Example 16, wherein the at least one processor comprises: a first processing circuit disposed in an implantable medical device (IMD), the first processing circuit configured to determine the potential cardiac pause of the patient; and a second processing circuit disposed in the IMD, the second processing circuit configured to perform the validation check.

In an Example 25, a system comprises: a sensing component configured to be operatively coupled to a patient and to obtain values of a first physiological parameter, wherein the values of the first physiological parameter are values of an electrogram; a first processing circuit configured to: (1) identify a first R wave peak using a first electric potential threshold; (2) identify a second R wave peak using the first electric potential threshold; (3) determine, based on the first and second R wave peaks, a first R-R interval; and (4) determine a potential cardiac pause of the patient by determining that the first R-R interval is greater than a time threshold; and a second processing circuit configured to perform a validation check of the potential cardiac pause using at least one of the values of the first physiological parameter or values of a second physiological parameter.

In an Example 26, the system of Example 25, wherein the sensing component and at least one of the first processing circuit and second processing circuit are disposed in an implantable medical device (IMD).

In an Example 27, the system of Example 26, wherein the sensing component and at least one of the first processing circuit and the second processing circuit are disposed in a wearable medical device.

In an Example 28, the system of Example 25, wherein the sensing component and the first processing circuit are disposed in an implantable medical device (IMD), the system further comprising an external monitoring device (EMD) configured to be disposed outside the patient's body, the EMD comprising the second processing circuit.

In an Example 29, the system of Example 25, wherein the second processing circuit performs the validation check by (1) identifying, between the first and second R wave peaks, a third R wave peak using a second electric potential threshold; (2) determining a second R-R interval, based on the third R wave peak; and (3) determining whether the second R-R interval exceeds the time threshold.

In an Example 30, the system of Example 25, wherein the second processing circuit is configured to confirm the validation check by performing at least one of a: morphological analysis of the electrogram and a frequency analysis of the electrogram.

In an Example 31, the system of Example 25, the second physiological parameter comprising at least one of activity, posture, heart sounds and impedance.

In an Example 32, a method comprises: obtaining values of a first physiological parameter of a patient; determining, using the values of the first physiological parameter, a potential cardiac pause of the patient; and performing a validation check of the potential cardiac pause using at least one of the values of the first physiological parameter or values of a second physiological parameter.

In an Example 33, the method of Example 32, wherein determining the potential cardiac pause includes determining when a first R-R interval is greater than a time threshold, wherein an R wave of the first R-R interval is identified using a first electric potential threshold, and wherein performing the validation check includes determining a second R-R interval of the electrogram during the potential cardiac pause, the second R-R interval comprising an additional R wave, wherein the additional R wave is identified using a second electric potential threshold.

In an Example 34, the method of Example 33, wherein the first electric potential threshold is at least 33% greater than the second electric potential threshold.

In an Example 35, the method of Example 33, wherein performing the validation check includes using values obtained from at least one of: a second electrogram, an activity sensor, a posture sensor, a heart sound sensor and an impedance sensor.

While multiple embodiments are disclosed, still other embodiments of the present disclosure will become apparent to those skilled in the art from the following detailed description, which shows and describes illustrative embodiments of the disclosure. Accordingly, the drawings and detailed description are to be regarded as illustrative in nature and not restrictive.

While the disclosed subject matter is amenable to various modifications and alternative forms, specific embodiments have been shown by way of example in the drawings and are described in detail below. The intention, however, is not to limit the disclosure to the particular embodiments described. On the contrary, the disclosure is intended to cover all modifications, equivalents, and alternatives falling within the scope of the disclosure as defined by the appended claims.

As the terms are used herein with respect to ranges of measurements (such as those disclosed immediately above), "about" and "approximately" may be used, interchangeably, to refer to a measurement that includes the stated measurement and that also includes any measurements that are reasonably close to the stated measurement, but that may differ by a reasonably small amount such as will be understood, and readily ascertained, by individuals having ordinary skill in the relevant arts to be attributable to measurement error, differences in measurement and/or manufacturing equipment calibration, human error in reading and/or setting measurements, adjustments made to optimize performance and/or structural parameters in view of differences in measurements associated with other components, particular implementation scenarios, imprecise adjustment and/or manipulation of objects by a person or machine, and/or the like.

Although the term "block" may be used herein to connote different elements illustratively employed, the term should not be interpreted as implying any requirement of, or particular order among or between, various steps disclosed herein unless and except when explicitly referring to the order of individual steps. Additionally, a "set" or "group" of items (e.g., inputs, algorithms, data values, etc.) may include one or more items, and, similarly, a subset or subgroup of items may include one or more items.

DETAILED DESCRIPTION

Embodiments of the present disclosure relate to reducing false positives in detection of cardiac pauses. As mentioned above, a cardiac pause can be determined from QRS complexes by calculating the time interval between R waves of different QRS complexes (R-R interval). In embodiments, a potential cardiac pause may be determined if, after an R wave is identified, a subsequent R wave does not occur within a specified temporal distance. In embodiments, however, a cardiac pause may be incorrectly determined when the calculated time interval between R waves does not accurately reflect the physiological reality. This may occur, for example, when the cardiac pause is determined based on an R-R interval exceeding a threshold, but where the calculated R-R interval represents a time interval between R waves of QRS complexes that are not adjacent to one another, where the threshold is configured to be used with R-R intervals between adjacent QRS complexes.

Typically, medical systems identify R waves of a QRS complex by setting an electric potential threshold that will trigger the medical system to identify an R wave when the electric potential threshold is met or exceeded. If the electric potential threshold is not set high enough, T waves, P waves and/or noise may exceed the electric potential threshold. As such, many waves may be falsely identified as R waves. Alternatively, or additionally, if the electric potential threshold is set too high, some of the R waves may not be identified because their peak electric potential may fall below the threshold. Adding complexity to the problem of appropriately setting an electric potential threshold is the notion that the amplitudes of R waves may vary depending on a patient's posture, activity level, change in fluid volume, and/or the like. As such, while the amplitudes of a patient's R waves might generally exceed an electric potential threshold in one situation (e.g., while the patient is standing up), it does not follow that the patient's R waves will exceed the electric potential threshold in another situation (e.g., while the patient is lying down). Due, at least in part, to these, and similar, considerations, cardiac pauses are oftentimes incorrectly determined. Embodiments of this disclosure may facilitate reducing false positives for the detection of cardiac pauses.

Figure 1:
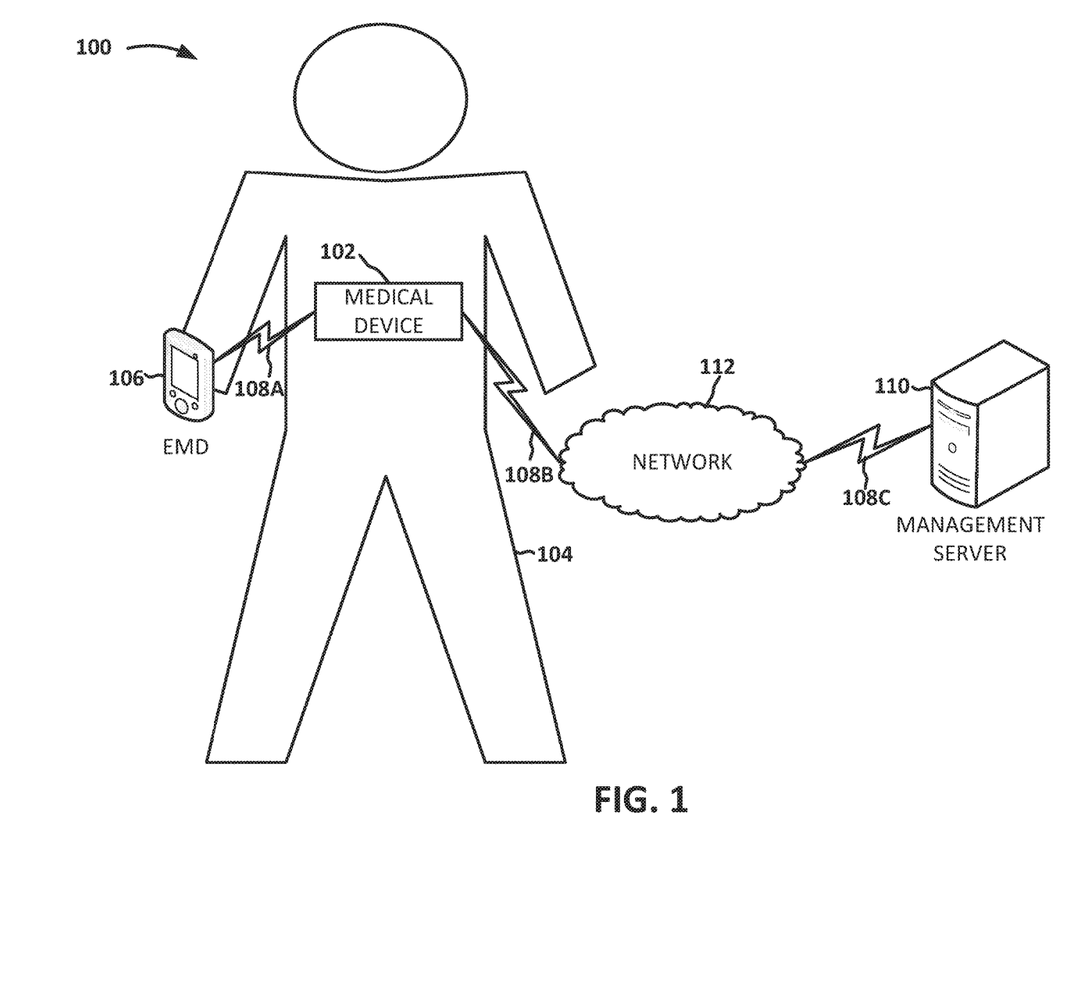
FIG. 1 is a schematic drawing of an illustrative medical system for reducing false positives in detection of potential episodes, in accordance with embodiments of the disclosure.

FIG. 1 shows an illustrative medical system 100, in accordance with embodiments of the disclosure. As shown in FIG. 1, the medical system 100 includes a medical device 102 operatively coupled to a subject 104. A medical device 102 that is operatively coupled to a subject includes one or more sensing components (e.g., sensors) capable of obtaining information from and/or about the subject, and/or one or more therapy components capable of providing therapy to the subject. In embodiments, sensor and/or therapy components may be disposed in, on, or near the subject, may be configured to operate in direct contact with the subject and/or without directly contacting the subject. In embodiments, for example, the medical device 102 may be external to the subject 104 or may be implanted in the subject 104. The medical system 100 also includes an external monitoring device (EMD) 106 that may, for example, be configured to be disposed outside of the subject's body 104, and may also, in embodiments, be operatively coupled to the subject 104. The subject 104 may be a human, a dog, a pig, and/or any other animal having physiological parameters that can be recorded. For example, in embodiments, the subject 104 may be a human patient. The medical device 102 may be communicatively coupled to the EMD 106 via a communication link 108A.

Additionally, the medical device 102 and/or the EMD 106 may communicate with a management server 110 via a network 112, as described below. In embodiments, the management server 110 may include any type of server device, server function, and/or server application configured to provide any type of service such as, for example, analysis, data storage, device provisioning, software updating, and/or the like. In embodiments, the management server 110 may be one server or multiple servers and may be accessible by any number of different types of users, devices, and/or the like.

Various components depicted in the system 100 may operate together with and/or incorporated into another monitoring system, which may be, for example, a computerized patient management and monitoring system. In embodiments, the system 100 may be designed to assist in monitoring the subject's condition, managing the subject's therapy, and/or the like. An illustrative patient management and monitoring system that utilizes embodiments of an EMD 106 and a management server 110 is the LATITUDE® patient management system from Boston Scientific Corporation, Natick Mass. Illustrative aspects of a patient management and monitoring system are described in ADVANCED PATIENT MANAGEMENT SYSTEM INCLUDING INTERROGATOR/TRANSCEIVER UNIT, U.S. Pat. No. 6,978,182 to Mazar et al., the entirety of which is hereby incorporated by reference herein.

The illustrative medical system 100 shown in FIG. 1 is not intended to suggest any limitation as to the scope of use or functionality of embodiments of the present disclosure. Neither should the illustrative medical system 100 be interpreted as having any dependency or requirement related to any single component or combination of components illustrated therein. Additionally, various components depicted in FIG. 1 may be, in embodiments, integrated with various ones of the other components depicted therein (and/or components not illustrated), all of which are considered to be within the ambit of the present disclosure.

According to embodiments, for example, the medical device 102 may include any type of medical device, any number of different components of an external medical device, any number of different components of an implantable system, and/or the like. In embodiments, one or more functions and/or components of the medical device 102, as described below, may be integrated into a single device as depicted in FIG. 1, or may be distributed between multiple devices, which may be implanted, worn, carried, and/or otherwise operatively coupled to the subject 104. That is, for example, the medical device 102 may be an implantable medical device (IMD) configured to be implanted within the body of the subject 104, may be configured to be outside of the subject's body 104, or may include one or more implantable components, one or more components configured to be outside of the body 104, and/or one or more transcutaneous components. In various embodiments, the medical device 102 may be a device that is configured to be portable with the subject 104, e.g., by being integrated into a vest, belt, harness, patch, sticker; placed into a pocket, a purse, or a backpack; carried in the subject's hand; and/or the like, or otherwise operatively (and/or physically) coupled to the subject 104.

Furthermore, the medical device 102 may be, or be incorporated into, another medical device. The medical device 102 may include a control device, a monitoring device, a pacemaker, an implantable cardioverter defibrillator (ICD), a cardiac resynchronization therapy (CRT) device and/or the like, and may be an implantable medical device configured for providing therapy and/or diagnostic data about the subject 104 and/or the medical device 102. In various embodiments, the medical device 102 may include both defibrillation and pacing/CRT capabilities (e.g., a CRT-D device). In embodiments, the medical device 102 may be implanted subcutaneously within an implantation location or pocket in the patient's chest or abdomen. For example, the medical device 102 may be an implantable cardiac monitor (ICM) (e.g., implantable diagnostic monitor (IDM), implantable loop recorder (ILR), etc.) and/or a subcutaneous implantable cardioverter defibrillator (S-ICD).

In embodiments, the medical device 102 may be used to gather data (e.g., measure, sense, record and/or receive data) associated with any number of a variety of physiological, subjective, and/or environmental parameters (collectively referred to herein as "parameters") associated with the subject 104, using electrical, mechanical, and/or chemical means. In embodiments, the medical device 102 may be configured to automatically gather data associated with parameters, gather data associated with parameters upon request (e.g., input provided by the subject, a clinician, another device, and/or the like), and/or any number of various combinations and/or modifications thereof.

For example, the medical device 102 may be configured to monitor (e.g., measure, sense and/or record) physiological parameters associated with the patient's heart. In embodiments, the medical device 102 may be configured to monitor physiological parameters associated with one or more other organs, systems, and/or the like. The medical device 102 may be configured to record physiological parameters such as, for example, one or more cardiac electrical signals, heart sounds, heart rate, oxygen saturations, and/or the like. In embodiments, the medical device 102 may also be configured to detect physiological parameters that may include one or more signals indicative of a patient's physical activity level (e.g., using an accelerometer), metabolic level and/or other parameters relating to human body, such as temperature (e.g., using a thermometer), blood pressure (e.g., using a sphygmomanometer), blood characteristics (e.g., glucose levels), body weight, physical strength, mental acuity, diet, relative geographic position (e.g., using a Global Positioning System (GPS)), and/or the like.

In addition, or alternatively, the medical device 102 may be configured to detect intrathoracic impedance, from which various respiratory parameters may be derived, including, for example, respiratory tidal volume and minute ventilation. As another example, the medical device 102 may be configured to detect one or more body movements or body postures and/or position related signals. For example, one or more accelerometers and/or GPS devices may be employed to detect patient activity, patient location, body orientation, torso position, and/or posture.

The medical device 102 may also be able to obtain information about the external environment (e.g., temperature, air quality, humidity, carbon monoxide level, oxygen level, barometric pressure, light intensity, sound, and/or the like) surrounding the patient 104, and/or the like (collectively referred to herein as "environmental parameters").

According to embodiments, the medical device 102 may also be configured to receive subjective and/or perceptive data from the subject 104 (collectively referred to herein as "subjective parameters"). A subjective parameter is information related to a patient's feelings, perceptions, and/or opinions, as opposed to, for example, objective physiological data. For example, the medical device 102 may be configured to receive subject responses to inquiries such as "How do you feel?" and "How is your pain?" The medical device 102 may be configured to prompt the subject 104 and record subjective data from the subject 104 using visual and/or audible cues. In embodiments, the subject 104 can press coded response buttons or type an appropriate response on a keypad or other touch interface included in the medical device and/or EMD 106, which may be, for example, a user device (e.g., a cell phone, programmer, laptop, etc.). In embodiments, subjective data may be collected by allowing the subject 104 to speak into a microphone and using speech recognition software to process the subjective data. In embodiments, the medical device 102 is configured to receive the subjective parameters. Alternatively, or in addition, the medical device 102 may be configured to receive subjective parameters via an EMD 106 that is communicatively coupled to the medical device 102 via the communication link 108A.

In embodiments, the medical device 102 may be configured to store data related to the sensed physiological, environmental, and/or subjective parameters. The medical device 102 may also be configured to transmit and/or receive the parameter data to any number of other devices in the system 100. The medical device 102 may be configured to sense, record and/or transmit at regular intervals, continuously, and/or in response to a detected event.

In embodiments, the medical device 102 may also be configured to deliver therapy to the subject 104. In embodiments, therapy may be provided automatically, for example, after performing additional analysis on a potential episode, and/or upon request (e.g., an input by the subject 104, a clinician, another device or process, and/or the like). In embodiments, the medical device 102 may be programmable in that various characteristics of sensing, analysis and therapy (e.g., duration and interval), respectively, may be altered by communication between the medical device 102 and other components of the system 100 (e.g., the EMD 106, the management server 110, etc.).

In embodiments, the communication link 108A (and other communication links 108B-108C discussed herein) may be, or include, a wired communication link and/or a wireless communication link such as, for example, a short-range radio link, such as Bluetooth, IEEE 802.11, a proprietary wireless protocol, and/or the like. In embodiments, for example, the communication link 108A may utilize Bluetooth Low Energy radio (Bluetooth 4.1), or a similar protocol, and may utilize an operating frequency in the range of 2.40 to 2.48 GHz. The term "communication link" may refer to an ability to communicate some type of information in at least one direction between at least two devices, and should not be understood to be limited to a direct, persistent, or otherwise limited communication channel. That is, according to embodiments, the communication link 108A may be a persistent communication link, an intermittent communication link, an ad-hoc communication link, and/or the like. The communication link 108A may refer to direct communications between the medical device 102 and other components of system 100 and/or indirect communications that travel between the medical device 102 and other components of the system 100 via at least one other device (e.g., a repeater, router, hub, and/or the like). The communication link 108A may facilitate uni-directional and/or bi-directional communication between the medical device 102 and other components of the system 100. Data and/or control signals may be transmitted between the medical device 102 and other components of the system 100 to coordinate the functions of the medical device 102 and other components of the system 100. In embodiments, patient data may be downloaded from other of the medical device 102 periodically or on command. The physician and/or the patient may communicate with the medical device 102, for example, to acquire patient data or to initiate, terminate and/or modify recording and/or therapy.

As shown, the medical device 102 may be configured to send data to, and receive data from, any number of other devices, depicted (e.g., the EMD 106, a management server 110, etc.) or not depicted in FIG. 1. Such communications may be transported over a network 112, for example, a local area network (LAN), via communication links 110B, 110C. In some embodiments, the medical device 102 may communicate directly with the management server 110, which may be located in the subject's home and/or at a remote location (e.g., the server 110 may be implemented, at least in part, as software having components instantiated by more than one device). The medical device 102 may also or alternatively incorporate multi-mode wireless telecommunications such as cellular, BLUETOOTH, or IEEE 802.11B to communicate with the network 112. For example, the medical device 102 may include a miniature cellular phone capable of wirelessly uploading clinical data from the device on a periodic basis. In addition, in embodiments, medical device 102 may function in a hybrid form, utilizing wireless communication when available and defaulting to a local wireless portal or a wired connection when the wireless communication becomes unavailable. The network 112 may be, or include, any number of different types of communication networks such as, for example, a bus network, a short messaging service (SMS), a local area network (LAN), a wireless LAN (WLAN), a wide area network (WAN), the Internet, a P2P network, custom-designed communication or messaging protocols, and/or the like. The network 112 may include a combination of multiple networks.

In embodiments, the medical device 102 may be configured to communicate during a given duty cycle. For example, the medical device 102 may be configured to communicate with the management server 110 (or other device) at given intervals, such as once a week. The medical device 102 may write data for the time period (e.g., a week) and transmit the data to the management server 110 (or other device) during the portion of the cycle that transmission is active and then conserve energy for the rest of the cycle. In another example, the medical device 102 may conserve energy and only communicate with the management server 110 (or other device) when a trigger event has occurred.

In embodiments, the medical device 102 may be configured to analyze parameter data gathered by the medical device 102. For example, the medical device 102 may be configured to determine a potential episode (e.g., a potential cardiac pause) and perform additional analysis on the episode (e.g., perform a validation check of the potential cardiac pause). In embodiments, the EMD 106 may be configured to perform the additional analysis. As it is used herein, the term "episode" refers to a time period during which some sort of abnormal or otherwise interesting event occurs. "Episode data" may include parameter data obtained before, during and/or after an episode, and may also include device settings, actions that were taken by the device, actions that were taken by a user, environmental parameters, and/or other information.

For example, an episode may be a potential cardiac pause of a patient's heart. That is, in embodiments, a determination algorithm may be incorporated into the medical device 102 to determine a potential cardiac pause based on one or more parameters. For example, a potential cardiac pause may be determined if an R-R interval, included in a patient's physiological parameter data, exceeds a time threshold. As another example, a potential cardiac pause may be determined if a subsequent R wave does not occur within a specified period of time after an identified occurrence of an R wave. In other words, a determination algorithm may be configured to identify an R wave in an electrogram, search for a subsequent R wave within a specified time period (that is, within a specified time window of the electrogram) and, if a subsequent R wave is not identified within that specified time window, the determination algorithm may determine that a potential cardiac pause occurred. In embodiments, the time threshold and/the specified temporal distance may be user-defined, system-defined, statistically-defined, dynamically-defined, and/or the like, and may include using one or more of the following: the patient's age, sex, temperature, blood pressure, body weight, physical strength, diet, heart characteristics, posture, hydration, physical activity level, metabolic level, heart sounds, mental acuity, relative geographic position, intrathoracic impedance, respiratory tidal volume, minute ventilation, subjective feelings and/or other parameters. As an example, the time threshold may be user-defined based on a baseline R-R threshold for the patient. That is, for example, if the patient normally exhibits an R-R interval of less than 3 seconds, a potential cardiac pause may be determined if an R-R interval, for the patient, is greater than or equal to 3 seconds. In some cases, the time threshold may be set (and/or adjusted) for all patients, for a group of patients, and/or the like.

In embodiments, the medical device 102 may perform additional analysis on the episode data, or part of the episode data, corresponding to a particular episode. For example, if a potential cardiac pause (i.e., an episode) is determined, the medical device 102 may perform a validation check (i.e., additional analysis) of the potential cardiac pause using the episode data (e.g., data corresponding to a time period during which the potential cardiac pause is determined to have occurred). According to embodiments, the determination algorithm may be configured to be more sensitive than the validation check, whereas the validation check may be configured to be more specific than the determination algorithm. In other words, the determination may have higher sensitivity while the validation may have higher specificity. As an example, assume an R-R interval exceeds a time threshold, which is indicative of a potential cardiac pause. Further assume that a first electric potential threshold is used to identify R waves used in calculating the R-R intervals. In response to determining the potential cardiac pause, a validation component incorporated into the medical device 102 may perform a validation check of the cardiac pause. In embodiments, a validation check may include determining a second R-R interval, where an R wave of the second R-R interval is identified using a second electric potential threshold that is less than the first electric potential threshold. For example, the first electric potential threshold may be 33% greater than the second electric potential threshold.

As another example, the validation component of the medical device 102 may perform a validation check based on the patient's posture. That is, when the medical device 102 senses that the patient using the medical device 102 is sitting and/or laying down, the validation check may determine that R waves are typically less than they otherwise would be (e.g. 10% less). If the first electric potential threshold is set to measure R waves when a patient is standing, the medical device 102 may implement a second electric potential threshold that is lower than the first electric potential threshold (e.g., 10% lower).

As another example, the validation component of the medical device 102 may perform a validation check based on one or more of the patient's heart sounds. For example, in response to determining a potential cardiac pause, the validation component of the medical device 102 may determine whether the medical device 102 (or another device operatively coupled to the patient that is configured to measure heart sounds) detected the presence of one or more heart sounds during the R-R interval that includes the potential cardiac pause. If one or more heart sounds were detected near a fiducial included in the R-R interval that includes the potential cardiac pause, the validation component of the medical device 102 may invalidate the potential cardiac pause as being a false positive. However, if one or more heart sounds were not detected near a fiducial included the R-R interval that includes the potential cardiac pause, the potential cardiac pause may be validated. In embodiments, the fiducial may be where an R wave was expected to occur (+/−10%, 20% and/or the like) in the R-R interval that includes the cardiac pause. In embodiments, where an R wave was expected to occur may be determined by, for example, a patient's average R-R interval or the patient's R-R interval before the R-R interval that includes the potential cardiac pause. In embodiments, the heart sounds may be S1, S2, S3 and/or S4 heart sounds.

In embodiments, the medical device 102 may perform the validation check on the entire R-R interval or a subinterval of the R-R interval that includes the potential cardiac pause. For embodiments that perform the validation check on a subinterval of the R-R interval, an average R-R interval may be determined for the patient using a patient's physiological parameter data. In embodiments, the average R-R interval may be based on the last N number of beats (e.g., 3 beats, 4 beats, 5 beats, 6 beats and/or the like) of the patient. By adding the average R-R interval to the time that the last R wave was identified, the time at which another R wave was expected to occur can be identified. Using the identified time that another R wave was expected to occur, the validation check may be performed for a period of time that is centered at and surrounding the identified time. In embodiments, the period of time surrounding the identified time may be a fixed time (e.g., +/−10 ms, 20 ms, 30 ms, and/or the like), may be a percentage (e.g., +/−5%, 10%, 15% and/or the like) of the average R-R interval or may be a percentage (e.g., +/−5%, 10%, 15% and/or the like) of the prior R-R interval. For example, if identified time at which another R wave was expected to occur is $t_1$, then the validation check may be performed for the interval ($t_1-t_0$, $t_1+t_0$), where $t_0$ is a period of time (e.g., a fixed time period, a percentage of the average R-R interval variability or a percentage of the prior R-R interval).

In embodiments, the first and second electric potentials may be may user defined, system defined, statistically defined, dynamically defined, and/or the like and may include using one or more of the following: the patient's age, sex, temperature, blood pressure, body weight, physical strength, diet, heart characteristics, posture, hydration, physical activity level, metabolic level, heart sounds, mental acuity, relative geographic position, intrathoracic impedance, respiratory tidal volume, minute ventilation, subjective feelings and/or other environmental parameters. In embodiments, when performing a validation check, the medical device 102 and/or EMD 106 may be configured to update the time threshold, the first electric potential threshold and/or the second electric potential threshold based on the additional analysis.

Additionally, machine-learning techniques may be employed to adapt the time threshold, the first electric potential threshold and/or the second electric potential threshold to more rapidly-changing scenarios such as, for example, the impact of adjusting to a new medication, the impact of a temporary adjustment in sleep schedule, the impact of the air quality in a particular location (e.g., outside vs. inside, downtown vs. at home, one city vs. another, etc.), the impact of an allergic reaction to an environmental stimulus, the impact of a psychological response to an increase or decrease in an amount of sunlight over the course of one or more days, the impact of a rapid change in barometric pressure, and/or the like. According to embodiments, adapting the time threshold, the first electric potential threshold and/or the second electric potential threshold may include adjusting one or more value ranges, adding or subtracting types of information to be considered (e.g., requiring additional, or fewer, inputs to the determination component and/or validation component of the medical device 102), adjusting weight applied to one or more inputs, adjusting error terms, adjusting boundary conditions, and/or the like.

In embodiments, when performing a validation check (e.g., using a second electric potential threshold that is less than the first electric potential threshold or using heart sounds), if another R wave is not identified, then a cardiac pause may be validated. However, if when the validation check is performed and an R wave is identified that was not originally identified using the first electric potential threshold, then additional analysis may be performed to confirm the presence of the identified R wave.

In embodiments, the additional analysis to confirm the presence of the identified R wave may be a morphological analysis and/or a frequency analysis of the identified R wave (and/or a portion of the waveform including the identified R wave). For example, the identified R wave may be matched to one or more templates to confirm the presence of the identified R wave. That is, if the identified R wave matches one or more templates, then the presence of the identified R wave may be confirmed and, therefore, the additional analysis may result in a conclusion that a cardiac pause did not actually occur. If, however, the identified R wave is not matched to one or more templates, then the presence of the identified R wave may have been misidentified and, therefore, the additional analysis may result in a conclusion that a cardiac pause may have occurred. In embodiments, the morphological analysis may use a stored template (or templates) that are representative of a QRS complex. In embodiments, the morphological analysis may use a dynamically extracted template from the patient's physiological parameter data. For example, a template may be extracted from one or both of the R waves that surround the identified pause.

Additionally or alternatively, in embodiments where the validation check is performed on a subinterval (as described above), the additional analysis may include using a second electric potential threshold to potentially identify R waves included in the R-R interval but were outside the subinterval. In embodiments, the amplitudes of any peaks found in the subinterval may be compared to any peaks found outside the subinterval. An identified R wave may have been misidentified if there are relatively small or absent peaks outside of the subinterval. Illustrative aspects of a confirming an identified R wave are described in IMPEDANCE WAVEFORM MONITORING FOR HEART BEAT CONFIRMATION, U.S. patent application Ser. No. 14/609,059 to Thakur et al., the entirety of which is hereby incorporated by reference herein.

Since the medical device 102 may be configured to send data to, and receive data from, any number of other devices, one or more functions of the medical device 102 described above (e.g., sensing parameter data, determining a potential episode and/or performing additional analysis of the potential episode) may be performed by another device (e.g., by the EMD 106 and/or by the management server 110). Offloading one or more functions to another device may increase the longevity of the medical device 102. That is, for example, the medical device 102 may be configured to detect a potential syncope, and upon detecting the potential syncope, may be configured to provide information to the EMD 106 and/or the management server 110, which may be configured to perform a validation check of the potential syncope.

In implementations in which the EMD 106 performs the validation check, the EMD 106 may request data from the medical device 102 that it can use in performing the validation check. In embodiments, the medical device 102 may provide that data to the EMD 106 even in the absence of a request therefrom. In implementations in which the management server 110 performs the validation check, the management server 110 may request data from the EMD 106 that it can use in performing the validation check. If the EMD 106 does not have the requested data stored, the EMD 106 may first obtain the data from the medical device 102, and then provide the data to the management server 110. In embodiments, the medical device 102 may provide that data to the EMD 106, which may provide the data to the management server 110, even in the absence of a request therefrom.

In embodiments, for example, the EMD 106 may be a medical device and may include any one or more of the components, characteristics, features, and/or functionality of a medical device (e.g., the medical device 102), as described herein. In embodiments, the EMD 106 may perform one or more of the following functions: (1) data storage; (2) data analysis; (3) data forwarding; (4) patient interaction; (5) patient feedback; and (6) data communications. For example, the EMD 106 may facilitate communications between the medical device 102 and a management server 110. The EMD 106 may, periodically or in real-time, interrogate and download into memory clinically relevant patient data. This data may include, for example, P and R-wave measurements, pacing, shocking events, lead impedances, pacing thresholds, battery voltage, capacitor charge times, ATR episodes with electrograms, tachycardia episodes with electrograms, histogram information, and/or any other clinical information necessary to ensure patient health and proper device function.

According to various embodiments of the disclosed subject matter, any number of the components depicted in FIG. 1 (e.g., the IMD 102, the EMD 106, and/or the management server 110) may be implemented on one or more computing devices. The computing device may include any type of computing device suitable for implementing aspects of embodiments of the disclosed subject matter. Examples of computing devices include specialized computing devices or general-purpose computing devices such "multi-parameter monitors," "workstations," "servers," "laptops," "desktops," "tablet computers," "hand-held devices," "general-purpose graphics processing units (GPGPUs)," and the like, all of which are contemplated within the scope of FIG. 1, with reference to various components of the system 100 and/or computing device.

In embodiments, a computing device includes a bus that, directly and/or indirectly, couples the following devices: a processor, a memory, an input/output (I/O) port, an I/O component, and a power supply. Any number of additional components, different components, and/or combinations of components may also be included in the computing device. The I/O component may include a presentation component configured to present information to a user such as, for example, a display device, a speaker, a printing device, and/or the like, and/or an input component such as, for example, a microphone, a joystick, a satellite dish, a scanner, a printer, a wireless device, a keyboard, a pen, a voice input device, a touch input device, a touch-screen device, an interactive display device, a mouse, and/or the like.

The bus represents what may be one or more busses (such as, for example, an address bus, data bus, or combination thereof). Similarly, in embodiments, the computing device may include a number of processors, a number of memory components, a number of I/O ports, a number of I/O components, and/or a number of power supplies. Additionally any number of these components, or combinations thereof, may be distributed and/or duplicated across a number of computing devices.

In embodiments, memory includes computer-readable media in the form of volatile and/or nonvolatile memory and may be removable, nonremovable, or a combination thereof. Media examples include Random Access Memory (RAM); Read Only Memory (ROM); Electronically Erasable Programmable Read Only Memory (EEPROM); flash memory; optical or holographic media; magnetic cassettes, magnetic tape, magnetic disk storage or other magnetic storage devices; data transmissions; and/or any other medium that can be used to store information and can be accessed by a computing device such as, for example, quantum state memory, and/or the like. In embodiments, the memory stores computer-executable instructions for causing the processor to implement aspects of embodiments of system components discussed herein and/or to perform aspects of embodiments of methods and procedures discussed herein.

The computer-executable instructions may include, for example, computer code, machine-useable instructions, and the like such as, for example, program components capable of being executed by one or more processors associated with the computing device. Program components may be programmed using any number of different programming environments, including various languages, development kits, frameworks, and/or the like. Some or all of the functionality contemplated herein may also, or alternatively, be implemented in hardware and/or firmware.

Figure 2:
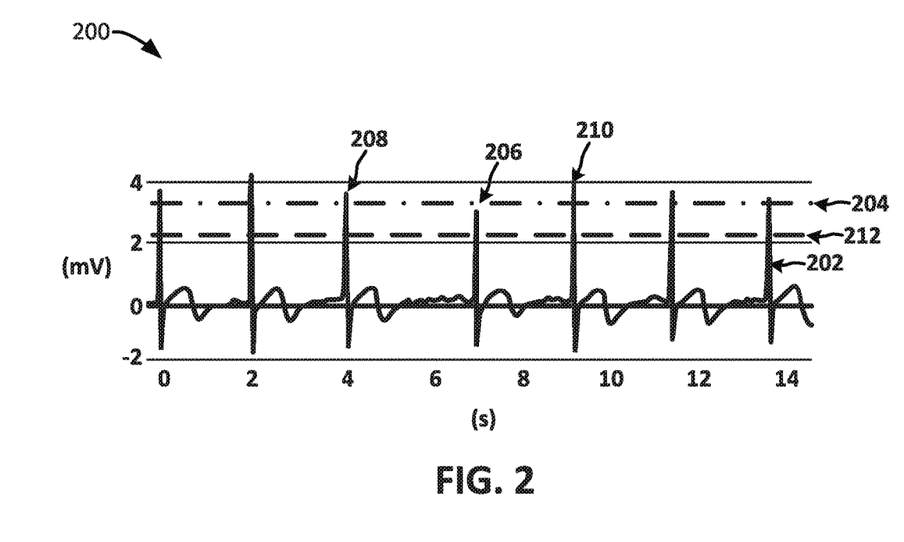
FIG. 2 is a graph depicting an illustrative potential episode and validation check of the potential episode, in accordance with embodiments of the disclosure.

FIG. 2 is a graph 200 depicting an illustrative potential cardiac pause and validation check, in accordance with embodiments of the disclosure. The graph 200 includes a plot of an EGM 202 of a patient. As discussed above, medical systems may include an electric potential threshold 204, which will identify an R wave of the EGM when the electric potential threshold 204 is met or exceeded. Furthermore, based on the differences between the times of the identified R waves, R-R intervals can be calculated for an EGM. If an R-R interval exceeds a time threshold, a potential cardiac pause and (e.g., associated with a syncope) can be identified. In embodiments, a potential cardiac pause may be determined if, after an R wave is identified, a subsequent R wave does not occur within a specified time period (e.g., time window of the electrogram).

As shown in FIG. 2, a first electric potential is set to approximately 3.7 mV. Accordingly, all R waves that exceed 3.7 mV will be identified. In this example, all the R waves in the EGM are identified except for the R wave 206. Since the R wave 206 is not identified, R wave 208 and R wave 210 are used to determine a first R-R interval. As shown, the first R-R interval is approximately 5 seconds. In this example, assume that the time threshold is greater than or equal to 4 seconds. Since the R-R interval is greater than 4 seconds, a potential cardiac pause is determined to have occurred for the patient.

In embodiments, to perform a validation check on the potential cardiac pause, a second R-R interval may be calculated using a second electric potential threshold 212 that is less than the first electric potential threshold 204. In embodiments, the first electric potential threshold 204 may be 33% greater than the second electric potential threshold. This is only an example, though, and is not meant to be limiting. Since the R wave 206 exceeds the second electric potential threshold 212, the validation check calculates a second R-R interval for the time interval between R wave 208 and R wave 206 that is approximately 3 seconds, and calculates a second R-R interval for the time interval between R wave 206 and R wave 210 that is approximately 2 seconds. Since both of these R-R intervals are less than the time threshold, the validation check determines the first R-R interval to be a false positive. In embodiments, if the validation check determined the same R-R interval, the validation check may determine the potential episode to be positive. As another example, the validation check may be performed using a morphological analysis, as discussed above in relation to FIG. 1. In embodiments, a medical system that performed a validation check may record, report and/or transmit the results, update the time threshold, the first electric potential and/or the second potential and/or provide alternative therapy (including not performing any therapy at all).

As discussed above with regard to FIG. 1, the time threshold, the first electric potential threshold 204 and the second electric potential 212 may be user-defined, system-defined, statically-defined, dynamically-defined, and/or the like, and may include using one or more of the following: the patient's age, sex, temperature, blood pressure, body weight, physical strength, diet, heart characteristics, posture, hydration, physical activity level, metabolic level, heart sounds, mental acuity, relative geographic position, intrathoracic impedance, respiratory tidal volume, minute ventilation, subjective feelings and/or other parameters.

Figure 3:
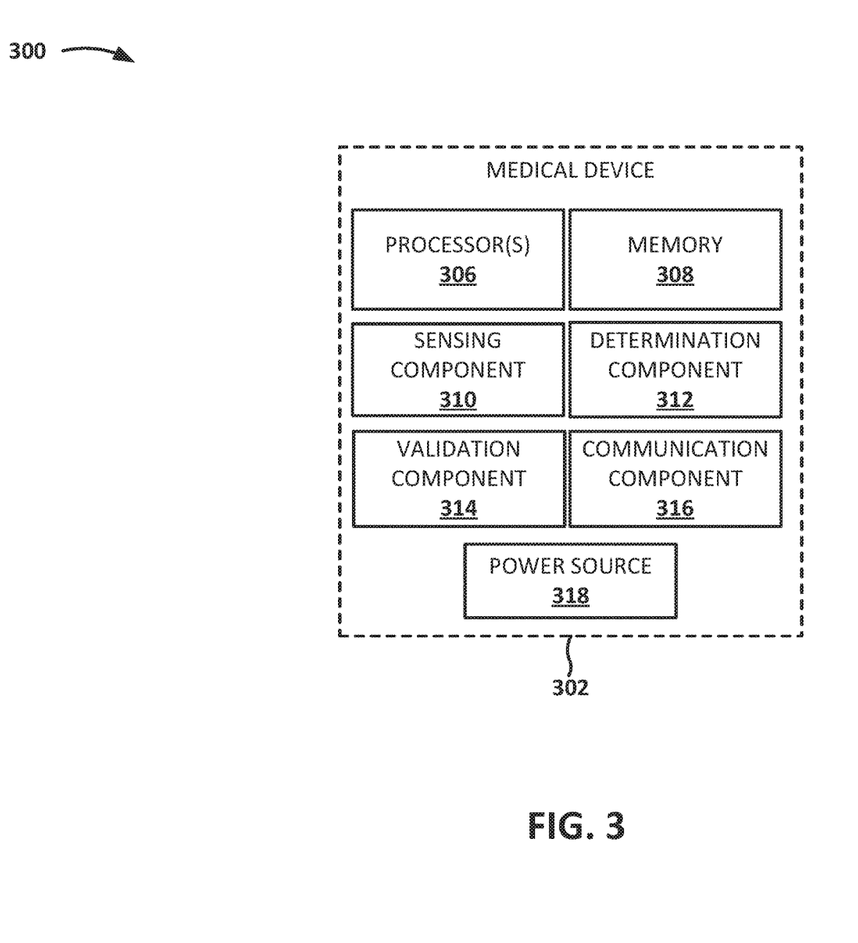
FIG. 3 is a block diagram of an illustrative medical device for reducing false positives in detection of potential episodes, in accordance with embodiments of the disclosure.

FIG. 3 is a block diagram depicting an illustrative system 300 for reducing false positives in detection of cardiac pauses, in accordance with embodiments of the disclosure. As shown, the system 300 includes a medical device 302. In embodiments, the medical device 302 may be, be similar to, include, or be included in, the medical device 102 depicted in FIG. 1, and/or the EMD 106 depicted in FIG. 1.

According to embodiments illustrated in FIG. 3, the medical device 302 includes a processor 306, memory 308, a sensing component 310, a determination component 312, a validation component 314, a communication component 316 and power source 318.

In embodiments, the processor 306 may include, for example, a processing device, a pulse generator, a controller, and/or the like. The processor 306 may be any arrangement of electronic circuits, electronic components, processors, program components and/or the like configured to store and/or execute programming instructions, to direct the operation of the other functional components of the medical device 302. For example, the processor 306 may control the storage of physiologic data obtained by the sensing component 310, control the determination component 312, control the validation component 314, control the communication component 316 and control the power source 318 and/or the like, and may be implemented, for example, in the form of any combination of hardware, software, and/or firmware.

In embodiments, the processor 306 may represent a single processor 306 or multiple processors 306, and the single processor 306 and/or multiple processors 306 may each include one or more processing circuits. In embodiments, the processor 306 may configured to be implanted in the patient and/or may be configured to be outside of the patient. That is, for example, the processor 306 may represent a component of an implantable medical device, an external medical device, and/or may represent at least one processor in an implantable medical device and at least one processor in an external device. The processor 306 may include one or more processing circuits, which may include hardware, firmware, and/or software. In embodiments, different processing circuits of the processor 306 may perform different functions. For example, the processor 306 may include a first processing circuit configured to determine a potential cardiac pause of a patient, and a second processing circuit configured to perform a validation check. That is, for example, the first processing circuit may be, include, and/or control the determination component 312, and the second processing circuit may be, include, and/or control the validation component 314. As such, using the example given in FIG. 2, the first processing circuit may identify R waves using a first electric potential threshold and the second processing circuit may identify R waves using a second electric potential.

The first processing circuit (or aspects thereof) and/or the second processing circuit (or aspects thereof) may be configured to be implanted in the patient and/or disposed external to the patient. That is, for example, in embodiments, the first processing circuit and the second processing circuit may be integrated within a processor 306 disposed in a medical device (e.g., an implantable medical device, an external medical device). In embodiments, the first processing circuit may be, or include, a first algorithm, virtual processor, and/or process implemented by the processor 306, and, similarly, the second processing circuit may be, or include, a second algorithm, virtual processor, and/or process implemented by the processor 306. In embodiments, the first processing circuit may be, or include, a first set of physical and/or virtual circuit elements, and, similarly, the second processing circuit may be, or include, a second set of physical and/or virtual circuit elements.

In embodiments, the processor 306 may be a programmable micro-controller or microprocessor, and may include one or more programmable logic devices (PLDs) or application specific integrated circuits (ASICs). In some implementations, the processor 306 may include memory as well. Although embodiments of the present system 300 are described in conjunction with a medical device 302 having a microprocessor-based architecture, it will be understood that the medical device 302 (or other device) may be implemented in any logic-based integrated circuit architecture, if desired. The processor 306 may include digital-to-analog (D/A) converters, analog-to-digital (A/D) converters, timers, counters, filters, switches, and/or the like. The processor 306 may execute instructions and perform desired tasks as specified by the instructions.

The processor 306 may also be configured to store information in the memory 308 and/or access information from the memory 308. The memory 308 may include volatile and/or non-volatile memory, and may store instructions that, when executed by the processor 306 cause methods (e.g., algorithms) to be performed by the medical device. In embodiments, the processor 306 may process instructions and/or data stored in the memory 308 to control sensing operations performed by the medical device 302, to control determination operations by the medical device 302, to control validation operations by the medical device 302, to control communications performed by the IMD 302 and/or the like.

The medical device 302 may sense physiological parameters using a sensing component 310 that may include, for example, one or more electrodes (not shown), one or more sensors (not shown), or a combination of these. In embodiments, the sensing component 310 may include any number of electrical circuits, electronic components, processors, program components and/or the like. The memory 308 may be used to store sensed information according to some implementations. Information from sense circuits included in the sensing component 310 may be used to determine a potential cardiac pause and/or perform a validation check of the potential cardiac pause.

In embodiments, the sensing component 310 may be configured to sense intrinsic cardiac electrical signals such as, for example, electrograms (EGMs) in a manner similar to known electrocardiogram (ECG) electrodes, which signals are transmitted via conventional techniques to the processor 306. In various embodiments, the sensing component 310 may be configured to sense other patient physiological and/or environmental parameters in addition to, or alternative to, cardiac signals. Examples of other physiological and environmental parameters may include, but are not limited to, the physiological, environmental and subjective parameters discussed above with regard to FIG. 1. The output from the sensing component 310 may be used in determining an episode, performing a validation check on an episode and/or the like.

In embodiments, the medical device 302 also includes a determination component 312 configured to determine a potential episode. The determination component 312 may be implemented in any combination of hardware, software, and/or firmware, and may be implemented, at least in part, by the processor 306.

The determination component 312 may determine a potential episode based on information received from any number of other components, devices, and/or the like. For example, the determination component 312 may obtain physiological, environmental and/or subjective parameter data from the sensing component 310 and may use that information to determine a potential episode. The episode criteria used to determine potential episodes may be may be user-defined (e.g., by a patient and/or a clinician), system-defined, statically-defined, dynamically-defined, and/or the like. The determination component 312 may reference episode criteria stored in memory (e.g., the memory 308) to determine whether a potential episode has occurred. As an example, the determination component 312 may determine cardiac pause, a specific type of episode, if the sensing component 310 senses an R-R interval that exceeds a time threshold, as described above with regard to FIGS. 1 and 2. In embodiments, a potential cardiac pause may be determined if, after an R wave is identified, a subsequent R wave does not occur within a specified temporal distance.

In embodiments, the medical device 302 also includes a validation component 314. The validation component 314 performs a validation check of a potential episode, as determined by the determination component 312. The validation component 314 may be implemented in any combination of hardware, software, and/or firmware, and may be implemented, at least in part, by the processor 306.

The validation component 314 may perform a validation check based on information received from any number of other components, devices, and/or the like. For example, the determination component 312 may obtain physiological, environmental and/or subjective parameter information from the sensing component 310 and may use that information to perform a validate check on a potential episode. The validation component 314 may reference validation criteria stored in memory (e.g., the memory 308) to perform a validation check.

As an example, to perform a validation check of a determined potential cardiac pause, the validation component 314 may be configured to receive the electrogram (EGM) data from the sensing component 310 and determine a second R-R interval, wherein a R wave of the second R-R interval is identified using a second electric potential threshold that is less than the electric potential threshold used to determine cardiac pause, as described in more detail with regard to FIGS. 1 and 2 above.

As another example, the validation component 314 may perform a validation check based on the patient's posture. For example, when the sensing component 310 senses that the patient using the medical device 302 is sitting and/or laying down, the validation check may determine that R waves are typically 10% less than they otherwise would be. If the first electric potential threshold is set to measure R waves when a patient is standing, the validation component 314 may implement a second electric potential threshold that is 10% lower than the first electric potential threshold.

As another example, the validation component 314 may perform a validation check based on one or more heart sounds of a patient, as described in related to FIG. 1 above. For example, in response to determining a potential cardiac pause, the validation component 314 may determine the presence of one or more heart sounds, during the R-R interval that includes the potential cardiac pause, were detected. If one or more heart sounds were detected near (e.g., +/−10%, 20% and/or the like) where an R wave should have registered, as determined by, for example, a patient's average R-R interval or the patient's R-R interval before the potential cardiac pause, the validation component 314 may dismiss the potential cardiac pause as being a false positive. However, if one or more heart sounds were not detected, the potential cardiac pause may be validated by the validation component 314.

As stated above with regard to FIG. 1, machine-learning techniques may be employed to adapt the time threshold, the first electric potential threshold and/or the second electric potential threshold. In embodiments, this may include adapting the time threshold, the first electric potential threshold and/or the second electric potential threshold to rapidly-changing scenarios such as, for example, the impact of posture, the impact of adjusting to a new medication, the impact of a temporary adjustment in sleep schedule, the impact of the air quality in a particular location (e.g., outside vs. inside, downtown vs. at home, one city vs. another, etc.), the impact of an allergic reaction to an environmental stimulus, the impact of a psychological response to an increase or decrease in an amount of sunlight over the course of one or more days, the impact of a rapid change in barometric pressure, and/or the like. According to embodiments, adapting the time threshold, the first electric potential threshold and/or the second electric potential threshold may include adjusting one or more value ranges, adding or subtracting types of information to be considered (e.g., requiring additional, or fewer, inputs), adjusting weight applied to one or more inputs, adjusting error terms, adjusting boundary conditions, and/or the like. In embodiments, after the medical device 302 performs a validation check, the results of the validation check may be confirmed, e.g., using morphological analysis, as described above in relation to FIG. 1. Additionally or alternatively, the medical device 302 may record, report and/or transmit the results, update the time threshold, the first electric potential and/or the second potential and/or provide alternative therapy (including not performing any therapy at all).

The communication component 316 included in the medical device 302 may include, for example, circuits, program components, and one or more transmitters, receivers, transceivers, transducers, and/or the like for communicating wirelessly with one or more other devices such as, for example, an external monitoring device (EMD) (e.g., the EMD 106 depicted in FIG. 1) and/or a server (e.g., the management server 110 depicted in FIG. 1). According to various embodiments, the communication component 316 may be configured to facilitate any number of different types of wireless communication such as, for example, radio-frequency (RF) communication, microwave communication, infrared communication, acoustic communication, inductive communication, conductive communication, and/or the like. The communication component 316 may include any combination of hardware, software, and/or firmware configured to facilitate establishing, maintaining, and using any number of communication links.

In embodiments, the communication component 316 of the medical device 302 facilitates wireless communication with other devices (e.g., the management server 110 depicted in FIG. 1) and other medical devices such as, for example, to facilitate coordinated operations between the medical devices. Since the medical device 302 may include a communication component 316 configured to send data to, and receive data from, any number of other devices, the sensing component 310, the determination component 312 and/or the validation component 314 may be performed by another device (e.g., by the EMD 106 and/or by the management server 110 depicted in FIG. 1).

The power source 320 included in the medical device 302 provides electrical power to the other operative components (e.g., the processor 306, the memory 308, the sensing component 310, the determination component 312, the validation component 314, and the communication component 316), and may be any type of power source suitable for providing the desired performance and/or longevity requirements of the medical device 302. In various embodiments, the power source 320 may include one or more batteries, which may be rechargeable (e.g., using an external energy source). The power source 320 may include one or more capacitors, energy conversion mechanisms, and/or the like. Power sources for medical devices such as the medical devices 302 are well known, and are therefore not discussed in greater detail herein.

The illustrative medical system 300 shown in FIG. 3 is not intended to suggest any limitation as to the scope of use or functionality of embodiments of the present disclosure. Neither should the illustrative medical system 300 be interpreted as having any dependency or requirement related to any single component or combination of components illustrated therein. Additionally, various components depicted in FIG. 3 may be, in embodiments, integrated with various ones of the other components depicted therein (and/or components not illustrated), all of which are considered to be within the ambit of the present disclosure.

Figure 4:
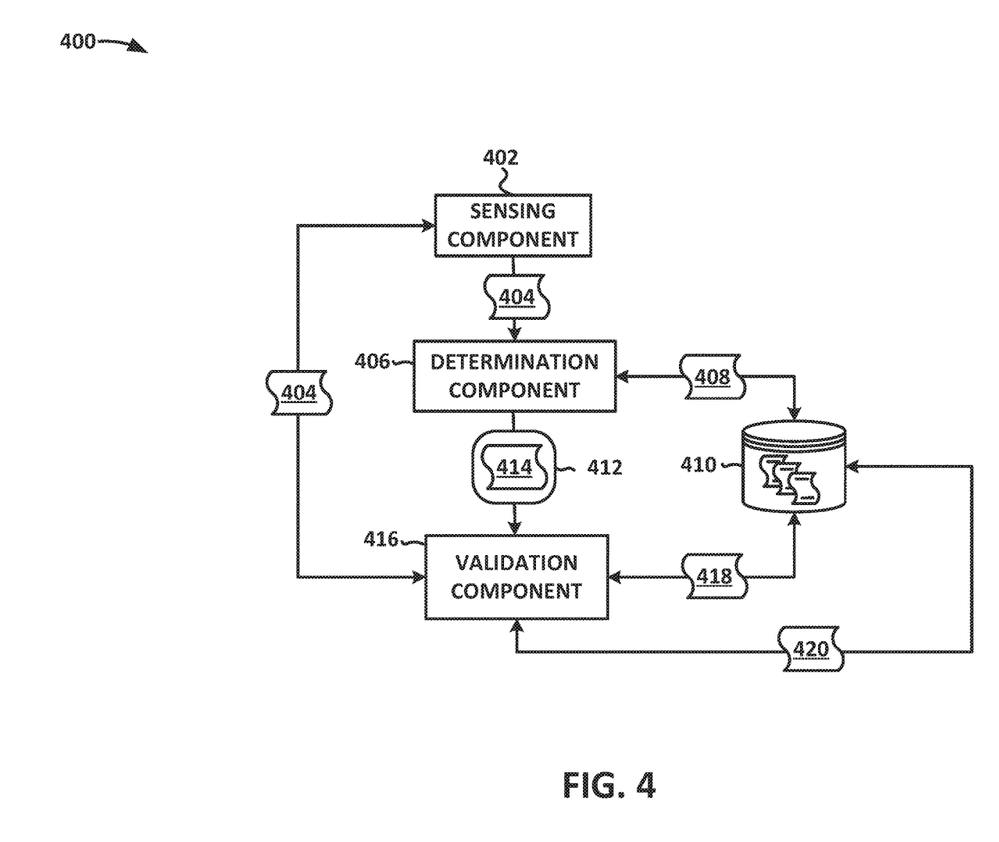
FIG. 4 is a schematic block diagram of an illustrative process for reducing false positives in detection of potential episodes, in accordance with embodiments of the disclosure.

FIG. 4 is a schematic diagram depicting an illustrative process flow 400 for reducing false positives in detection of cardiac pauses, in accordance with embodiments of the disclosure. Because any number of the various components depicted in FIG. 4 may be implemented in any number of different combinations of devices (such as, e.g., aspects of embodiments of the systems 100 and 300 depicted, respectively, in FIGS. 1 and 3), FIG. 4 is depicted, and described, without regard to the particular device(s) within which each component is implemented, but is rather discussed in the context of system components and their functions.

As shown in FIG. 4, the process flow 400 includes a sensing component 402 that obtains a set 404 of values of one or more physiological, environmental and/or subjective parameters and provides that set 404 of values to a determination component 406. In embodiments, the sensing component 402 may be, be similar to, include, or be included in, the sensing component 310 depicted in FIG. 3, and may be implemented, for example, in a medical device (e.g., the medical device 102 depicted in FIG. 1 and/or the medical device 302 depicted in FIG. 3). The physiological, environmental and/or subjective parameters may include, but are not limited to, the physiological, environmental and/or subjective parameters discussed above in the discussion of FIG. 1. For example, the set 404 may include an EGM for a patient.

In embodiments, the determination component 406 analyzes the set 404 to determine whether or not a potential episode (e.g., cardiac pause) has occurred using a set of episode criteria 408, which may retrieved from a memory 410. In embodiments, the determination component 406 may be, be similar to, include, or be included in, the determination component 312 depicted in FIG. 3, and may also, or alternatively, be implemented in an medical device (e.g., the medical device 102 depicted in FIG. 1 and/or the medical device 302 depicted in FIG. 3) and/or a server (e.g., the management server 110 depicted in FIG. 1). In embodiments, the episode criteria 408 for determining a potential episode may be or be similar to the episode criteria discussed above in the discussion of FIG. 3. For example, a potential episode may be determined if an R-R interval is greater than a time threshold. In embodiments, a potential cardiac pause may be determined if, after an R wave is identified, a subsequent R wave does not occur within a specified temporal distance. Moreover, in embodiments, the memory 410 may be, be similar to, include, or be included in, the memory 308 depicted in FIG. 3. The memory 410 may also, or alternatively, be implemented in a medical device and/or a server.

In embodiments, the determination component 406 may be configured to provide a notification 412 of a determined potential episode 414 to the validation component 416. The validation component 416 is configured to perform a validation check of the potential episode 414.

In embodiments, the validation component 416 may be, be similar to, include, or be included in, the validation component 314 depicted in FIG. 3, and may also, or alternatively, be implemented in a medical device and/or a server. To perform the validation check, the validation component 416 may request the set 404 from the sensing component 402 and/or validation criteria 418, which may be retrieved from the memory 410. In embodiments, the validation criteria 418 for determining a potential episode may be or be similar to the episode criteria discussed above in the discussion of FIG. 3. For example, the validation criteria 418 may include a second electric potential threshold that is used to identify R waves, such that the second electric potential threshold is less than the first electric potential threshold used to initially determine the R-R interval. As another example, the validation criteria 418 may use heart sounds to perform a validation check of a potential cardiac pause, as described in relation to FIGS. 1 and 3 above. In embodiments, the validation component 418 may also include confirm the results of the validation check, e.g., using morphological analysis, as described above in relation to FIG. 1.

In embodiments, the validation component 418 may be configured to send the results 420 of the validation check back to memory 410. In embodiments, the process flow 400 may include the machine-learning techniques may be employed based on the results 420 to adapt the episode criteria 408 and the validation criteria 418. In embodiments, this may include adapting the time threshold of the episode criteria 408, the first electric potential threshold of the episode criteria 408 and/or the second electric potential threshold of the validation criteria 418 to rapidly-changing scenarios such as, for example, the impact of posture, the impact of adjusting to a new medication, the impact of a temporary adjustment in sleep schedule, the impact of the air quality in a particular location (e.g., outside vs. inside, downtown vs. at home, one city vs. another, etc.), the impact of an allergic reaction to an environmental stimulus, the impact of a psychological response to an increase or decrease in an amount of sunlight over the course of one or more days, the impact of a rapid change in barometric pressure, and/or the like. According to embodiments, the episode criteria 408 and the validation criteria 418 may include adjusting one or more value ranges, adding or subtracting types of information to be considered (e.g., requiring additional, or fewer, inputs), adjusting weight applied to one or more inputs, adjusting error terms, adjusting boundary conditions, and/or the like.

Figure 5:
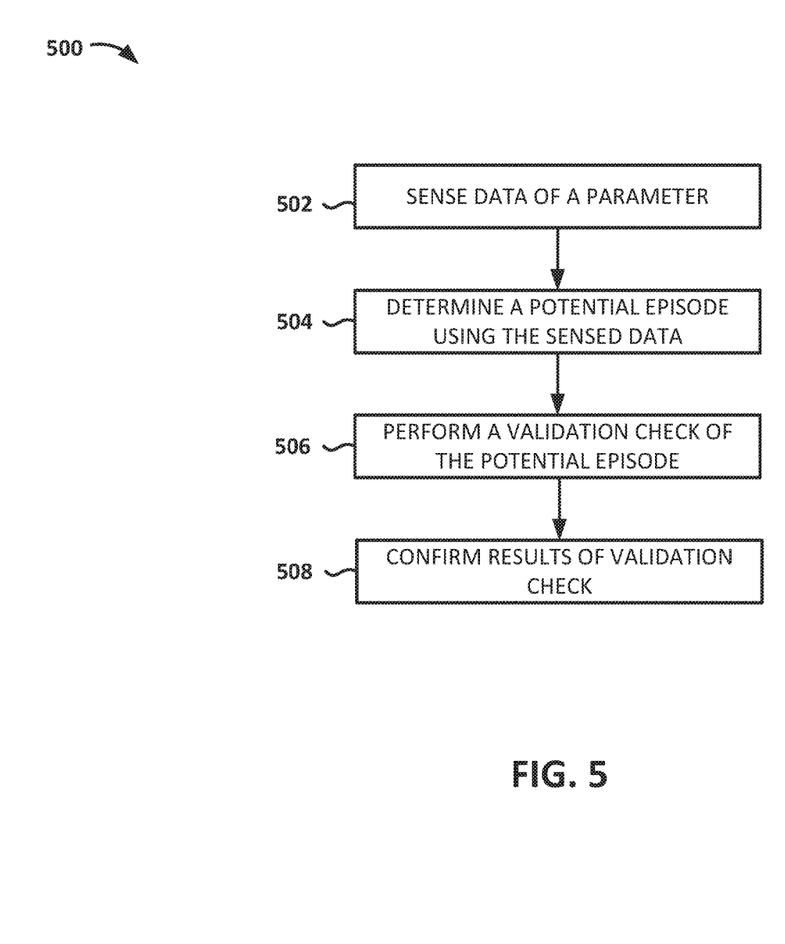
FIG. 5 is a flow diagram depicting an illustrative method for reducing false positives in detection of potential episodes, in accordance with embodiments of the disclosure.

FIG. 5 is a flow diagram depicting an illustrative method 500 for reducing false positives in detection of episodes. Embodiments of the method 500 may be performed by one or more components of a patient monitoring system such as, for example, the medical system 100 depicted in FIG. 1, the medical system 300 depicted in FIG. 3, using a process such as, for example, the illustrative process 400 depicted in FIG. 4.

Embodiments of the illustrative method 500 include sensing data corresponding to a parameter (block 502) (e.g., obtaining values of a physiological parameter). The sensing may be performed by a medical device (e.g., the medical device 102 depicted in FIG. 1 and/or the medical device 302 depicted in FIG. 3). The parameter that is sensed may include any number of different types of information such as, for example, physiological parameter values, environmental parameters, subjective parameters and/or the like discussed above in relation to FIG. 1. In embodiments, the data corresponding to the first parameter include cardiac electrical activity and, more specifically, QRS complexes for a patient.

The method 500 further includes determining a potential episode using the sensed data (block 504). Determining a potential episode may be performed by a medical device (e.g., the medical device 102 depicted in FIG. 1 and/or the medical device 302 depicted in FIG. 3), an external monitoring device (EMD) (e.g., the EMD 106 depicted in FIG. 1), and/or a server (e.g., the management server 110 depicted in FIG. 1). In embodiments, a potential episode may be determined if a set of episode criteria is met. In embodiments, the episode criteria can include, but is not limited to, the episode criteria discussed above. For example, determining a potential episode may include determining a potential cardiac pause. Specifically, the episode criteria may include determining if an R-R interval exceeds a time threshold. In embodiments, a first electric potential threshold may be used to identify R waves, in an ECG of a patient, that are used in computing the R-R interval. In embodiments, a potential cardiac pause may be determined if, after an R wave is identified, a subsequent R wave does not occur within a specified temporal distance. In embodiments, a single device can perform blocks 502 and 504. In embodiments, different devices can perform blocks 502 and 504, respectively.

The method 500 further includes performing a validation check of the potential episode (block 506). Performing a validation check may be performed by a medical device (e.g., the medical device 102 depicted in FIG. 1 and/or the medical device 302 depicted in FIG. 3), an external monitoring device (EMD) (e.g., the EMD 106 depicted in FIG. 1), and/or a server (e.g., the management server 110 depicted in FIG. 1). In embodiments, a validation check may be performed using a set validation criteria. In embodiments, the validation criteria can include, but is not limited to, the validation criteria discussed above. For example, performing a validation check may include determining a second R-R interval using a second electric potential threshold to identify R waves, in an EGM of a patient, wherein the second electric potential threshold is less than the first electric potential threshold. In embodiments, a single device can perform blocks 502, 504 and 506. In embodiments, different devices can perform one or more of blocks 502, 504, 506, respectively. As another example, a validation check may be performed using heart sounds. In embodiments, the validation check may be performed using heart sounds as described in relation to FIGS. 1 and 3 above.

In embodiments, method 500 further includes confirming the results of the validation check (block 508). In embodiments, the results of the validation check may be confirmed by a morphological analysis, e.g., the morphological analysis described above in relation to FIG. 1.

Various modifications and additions can be made to the exemplary embodiments discussed without departing from the scope of the present disclosure. For example, while the embodiments described above refer to particular features, the scope of this disclosure also includes embodiments having different combinations of features and embodiments that do not include all of the described features. Accordingly, the scope of the present disclosure is intended to embrace all such alternatives, modifications, and variations as fall within the scope of the claims, together with all equivalents thereof.

We claim:

1. A system comprising:
a sensing component configured to be operatively coupled to a patient and to obtain values of a first physiological parameter; and
at least one processor configured to:
determine a potential cardiac pause of the patient using the values of the first physiological parameter and at least one episode criterion;
perform a validation check of the potential cardiac pause using at least one validation criterion and at least one of: the values of the first physiological parameter or values of a second physiological parameter; and
adapt, in response to the validation check, at least one of the at least one episode criterion and the at least one validation criterion.

2. The system of claim 1, wherein the values of the first physiological parameter are values of an electrogram.

3. The system of claim 2, wherein the potential cardiac pause is determined when at least one of the following occurs: (1) a first R-R interval of the electrogram is greater than a time threshold, wherein the first R-R interval is identified using a first electric potential, or (2) a subsequent R wave does not occur within a specified period of time after an R wave is identified, wherein the R wave is identified using the first electric potential threshold.

4. The system of claim 3, wherein the at least one processor performs the validation check by calculating a second R-R interval and wherein an R wave of the second R-R interval is identified using a second electric potential threshold, the second electric potential threshold being less than the first electric potential threshold.

5. The system of claim 1, wherein the values of the second physiological parameter are obtained from a heart sound sensor and wherein the at least one processor performs the validation check by determining whether the second physiological parameter includes values indicative of heart sounds following a fiducial of the first physiological parameter.

6. The system of claim 5, wherein the heart sounds include at least one of: an S1 heart sound, an S2 heart sound, an S3 heart sound and an S4 heart sound.

7. The system of claim 1, wherein the at least one processor is configured to confirm the validation check by performing at least one of: a morphological analysis of the electrogram and a frequency analysis of the electrogram.

8. The system of claim 1, wherein the values of the second physiological parameter are obtained from at least one of the following: a second electrogram, an activity sensor, a posture sensor, a heart sound sensor and an impedance sensor.

9. The system of claim 1, wherein the at least one processor comprises:
a first processing circuit disposed in an implantable medical device (IMD), the first processing circuit configured to determine the potential cardiac pause of the patient; and
a second processing circuit disposed in the IMD, the second processing circuit configured to perform the validation check.

10. A system comprising:
a sensing component configured to be operatively coupled to a patient and to obtain values of a first physiological parameter, wherein the values of the first physiological parameter are values of an electrogram;
at first processing circuit configured to: (1) identify a first R wave peak using a first electric potential threshold; (2) identify a second R wave peak using the first electric potential threshold; (3) determine, based on the first and second R wave peaks, a first R-R interval; and (4) determine a potential cardiac pause of the patient by determining that the first R-R interval is greater than a time threshold; and
a second processing circuit configured to perform a validation check of the potential cardiac pause using at least one validation criterion and at least one of the values of the first physiological parameter or values of a second physiological parameter;
wherein at least one of the first processing circuit and the second processing circuit is configured to adapt, in response to the validation check, at least one of the first electric potential threshold, the time threshold, and the at least one validation criterion.

11. The system of claim 10, wherein the sensing component and at least one of the first processing circuit and second processing circuit are disposed in an implantable medical device (IMD).

12. The system of claim 11, wherein the sensing component and at least one of the first processing circuit and the second processing circuit are disposed in a wearable medical device.

13. The system of claim 10, wherein the sensing component and the first processing circuit are disposed in an implantable medical device (IMD), the system further comprising an external monitoring device (EMD) configured to be disposed outside the patient's body, the EMD comprising the second processing circuit.

14. The system of claim 10, wherein the second processing circuit performs the validation check by (1) identifying, between the first and second R wave peaks, a third R wave peak using a second electric potential threshold; (2) determining a second R-R interval, based on the third R wave peak; and (3) determining whether the second R-R interval exceeds the time threshold.

15. The system of claim 10, wherein the second processing circuit is configured to confirm the validation check by performing at least one of a: morphological analysis of the electrogram and a frequency analysis of the electrogram.

16. The system of claim 10, the second physiological parameter comprising at least one of activity, posture, heart sounds and impedance.

17. A method comprising:
  obtaining values of a first physiological parameter of a patient;
  determining, using the values of the first physiological parameter and at least one episode criterion, a potential cardiac pause of the patient;
  performing a validation check of the potential cardiac pause using at least one validation criterion and at least one of the values of the first physiological parameter or values of a second physiological parameter; and
  adapting, in response to the validation check, at least one of the at least one episode criterion and the at least one validation criterion.

18. The method of claim 17, wherein determining the potential cardiac pause includes determining when a first R-R interval is greater than a time threshold, wherein an R wave of the first R-R interval is identified using a first electric potential threshold, and wherein performing the validation check includes determining a second R-R interval of the electrogram during the potential cardiac pause, the second R-R interval comprising an additional R wave, wherein the additional R wave is identified using a second electric potential threshold.

19. The method of claim 18, wherein the first electric potential threshold is at least 33% greater than the second electric potential threshold.

20. The method of claim 18, wherein performing the validation check includes using values obtained from at least one of: a second electrogram, an activity sensor, a posture sensor, a heart sound sensor and an impedance sensor.

* * * * *